(12) United States Patent
von Kraus et al.

(10) Patent No.: US 10,130,287 B2
(45) Date of Patent: Nov. 20, 2018

(54) HEARING TEST SYSTEM

(71) Applicant: Audicus, Inc., New York, NY (US)

(72) Inventors: Lee M von Kraus, New York, NY (US); Patrick Freuler, New York, NY (US)

(73) Assignee: Audicus, Inc., New York, NY (US)

( * ) Notice: Subject to any disclaimer, the term of this patent is extended or adjusted under 35 U.S.C. 154(b) by 901 days.

(21) Appl. No.: 14/546,574

(22) Filed: Nov. 18, 2014

(65) Prior Publication Data

US 2016/0135719 A1 May 19, 2016

(51) Int. Cl.
*A61B 5/12* (2006.01)
*A61B 19/00* (2006.01)
*A61B 5/16* (2006.01)
*A61B 5/00* (2006.01)

(52) U.S. Cl.
CPC .............. *A61B 5/123* (2013.01); *A61B 5/165* (2013.01); *A61B 5/7455* (2013.01); *A61B 19/5212* (2013.01); *A61B 5/0022* (2013.01); *A61B 5/168* (2013.01); *A61B 5/6898* (2013.01); *A61B 5/74* (2013.01); *A61B 5/742* (2013.01); *A61B 5/7475* (2013.01)

(58) Field of Classification Search
CPC .................................. A61B 5/121; A61B 5/12
See application file for complete search history.

(56) References Cited

U.S. PATENT DOCUMENTS

| | | | |
|---|---|---|---|
| 6,496,585 B1 | 12/2002 | Margolis | |
| 7,704,216 B2 | 4/2010 | Margolis | |
| 2009/0112621 A1* | 4/2009 | Jung | ...................... G06F 19/328 705/2 |

* cited by examiner

*Primary Examiner* — Daniel Cerioni
*Assistant Examiner* — Yasmeen S Warsi
(74) *Attorney, Agent, or Firm* — Lee & Hayes, PLLC

(57) ABSTRACT

Techniques are described for improving results of hearing tests. For example, the hearing tests described herein may be divided into multiple hearing test segments which may be provided to the test subject individually. Additionally, the hearing test may include multiple cognitive test segments that may be interleaved between the hearing test segments to gauge the test subject's awareness level.

20 Claims, 8 Drawing Sheets

HEARING TEST SYSTEM

BACKGROUND

Audiometers have been used to test human hearing for many years. Hearing tests are typically performed in a sound proof room at a location where a hearing health professional is present. These tests typically include outputting to a user a series of tones or other parts of speech which are intended to elicit a user response. For example, many audiometers include a haptic input device to allow the test subject to click or select a button when a tone or part of speech is heard.

Unfortunately, many hearing tests may become predictable as the t timing of test stimuli becomes known to the test subject. Additionally, in some cases, the test becomes tedious as similar tones at various frequencies are repeated. Thus, the test subject may become bored or distracted resulting in less accurate responses by the test subject to audio stimuli, and therefore less accurate test results.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

DETAILED DESCRIPTION

Figure 1:
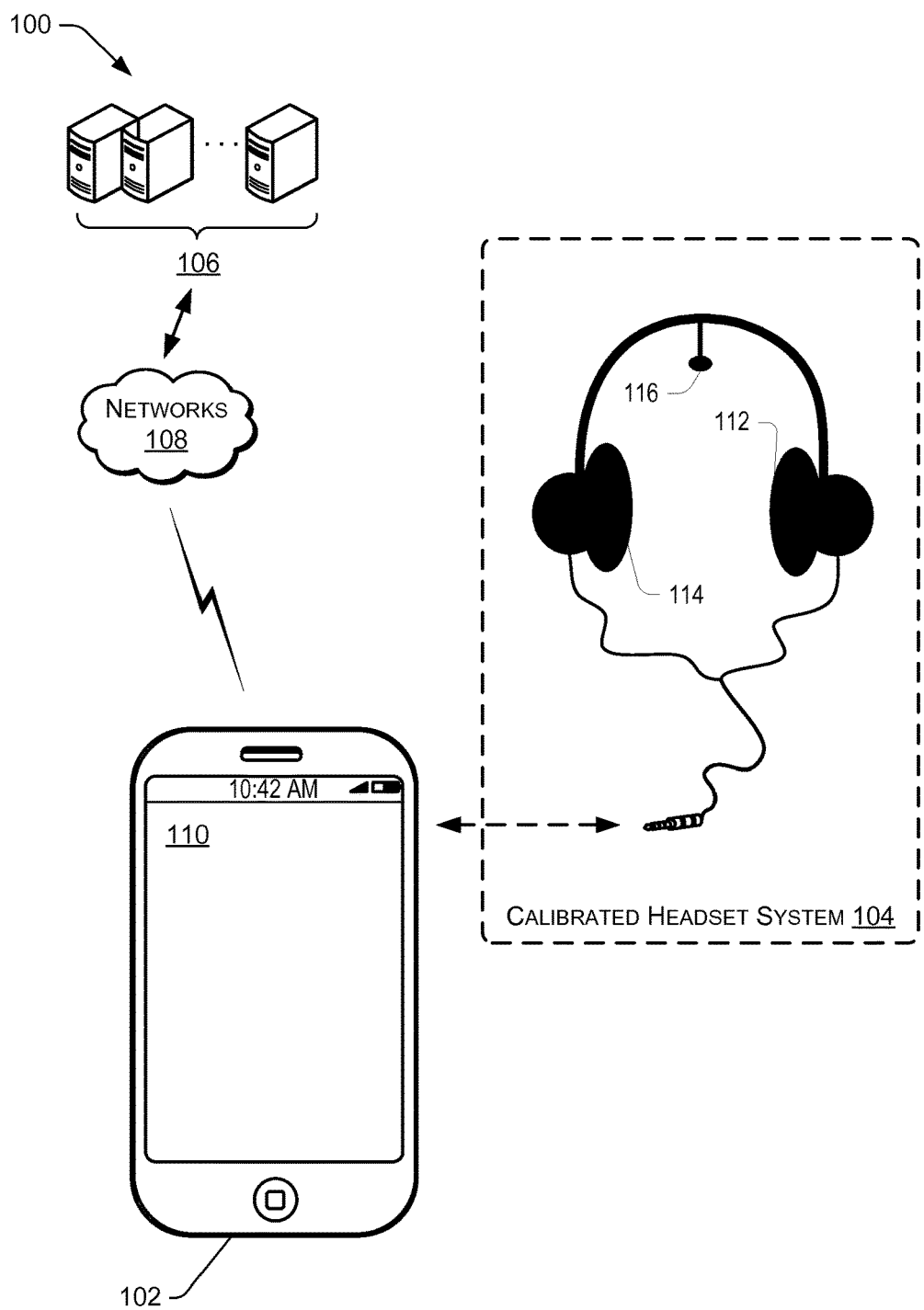
FIG. 1 illustrates an example hearing test system according to some implementations.

This disclosure includes techniques and implementations to improve accuracy of hearing related test results. In particular, this disclosure describes ways to improve the accuracy of test subject's responses during a hearing test. For instance, in some implementations described herein, the hearing test may be divided or broken down into test segments, for instance based on frequency ranges. In these implementations, the test device may interleave hearing test segments with cognitive or awareness based segments to improve the accuracy of the user responses when the test tones or other hearing related test segments are output.

In some examples, the test subject may show improvements in test accuracy and results as the test subject gains experience taking and responding to, for example, the test tones. In these examples, some of the implementations described herein, may include a test system configured to repeat hearing test segments to ensure the user was properly attentive and/or engaged at the time the test results are collected. For instance, the test system may be configured to identify, based on the test results of either the hearing test segments or a cognitive test segment preceding or following the hearing test segment that the test subject was attentive and engaged and the test results are accurate. In another instance, the test system may determine the test subject's clicks or responses were at a particular cadence, repetitiveness, or inconsistency indicating the test subject was not engaged with the test.

In these instances, the test system may repeat the particular hearing tests segment or interleave the hearing tests segment back into the hearing test at a later time. In some implementations, the test system may be configured to re-test a predetermined number of test segments to provide the test subject with a period of time to adjust to the particulars of the hearing test. In this manner, the test system is able to test the accuracy of previous results and/or to better ensure that the test subject has gained sufficient experience to provide accurate results. In some particular implementations, the test system may be configured to compare results of the past hearing test segments and/or cognitive test segments to determine if the test subject is engaged. For instance, this could be done when the results of an individual test is indicative of a distracted test taker.

In some instances, prior to beginning a hearing test or at various periods of time during the hearing tests, the test system may request the test subject to score a wakefulness and/or level of focus. For example, the test subject may select a level of focus based on a visual analog scale (VAS) or slide a bar on a display or user interface. In other instances, the test system may apply a Karolinsky Wakefulness test. In one particular instance, the test system may measure an awareness, wakefulness, and/or level of focus by outputting visual/audio/tactile stimulus and measuring the test subject's responsiveness. For example, by measuring a period of time between presenting a stimulus to the test subject and reviving a user input in response.

In some implementations, the test system described herein may be designed to be administered by a hearing health professional. However, in other implementations, the test system may be designed as an at home or test subject driven test. When the test system is designed as an at home test or test subject driven, the test system may include various features for improving the results. For example, the test system may be configured to instruct the test subject to place the sound damping foam of an in-ear earphones into the ear or to place over-the-ear headphones by following an instructional video or verbal steps. Once the foam is inserted by the test subject, the test system may be configured to play a tone, set of tones, particular sound or series of sounds, and/or melodies or songs within a frequency range the sound damping foam is intended to block or prevent the test subject from hearing. In this example, the test system may ask the test subject to confirm that no sounds were heard after the placement of the sound damping foam.

In some examples, the volumes of sounds used in a test would be chosen according to some measure or approximation of the subjects hearing abilities. For instance scores from a previous hearing test or average hearing abilities of people similar to the test subject (for instance, in terms of age, gender, etc.). For instance, in the former case this test could be performed after our hearing test is complete, to provide the app and the test-subject knowledge as to whether the previously obtained scores were obtained while the in-ear earphone sound dampening foam was properly inserted, or not.

In some particular implementations, the tests system may also be configured to provide a clock or timer associated with a period of time assigned to the test subject for the placement of the sound damping foam and/or a calibrated headset system for outputting the tones and other sounds assorted with a hearing test. For instance, in some cases, it may be necessary to place the sound damping foam within the ear canal within a predefined period of time. For example, the foam may be configured to begin expanding once released from the test subject's finger compression to more efficiently block outside noises (i.e. not originating from the earphone actuator) from entering the ear canal. In this case it is important to insert the compressed, small-diameter foam deeply into the ear canal before it has expanded to the extent that deep insertion is no longer possible, for example, in less than ten seconds. In these implementations, the test system may be configured to provide a visual and/or audio notification when the pre-defined period of time has elapsed. In this manner, the test subject may start over if the test subject was unable to place the foam within the ear canal within the predefined period of time.

In some examples, the test system may be equipped with one or more imaging technologies, such as a still or video camera. In this example, the test system may request or require the test subject to photograph or image both the test subject's right and left ear at various stages of the test setup using the imaging technologies. For example, after the placement of the sound damping foam (to which the earphone actuator may be attached), the test system may request the test subject to image both ears before allowing the test subject to proceed with the next step.

In some implementations, the test system may be configured to present the images of the test subject's ears including the foam and/or headset together with one or more images of correctly placed headsets. For example, the test system may present a fixed image of the test subject's right ear with the headset in place and cycle through a predefined number of images of other individuals with acceptable headset placements. The test system may ask the test subject to confirm via a user input that the test subject's foam and/or headset has been placed within acceptable margins.

In other implementations, the test system may analyze or process the images of the test subject's right and left ear to determine if the headset has been acceptably placed. For example, the test system may utilize one or more image processing techniques, such as color matching, blob analysis, signal processing, edge detection, scaling, filtering, among others. In some cases, the test system may determine the test subject has unacceptably placed the headset based on the image of the left and/or right ear. The test system may then re-instruct the test subject on the proper placement and cause the test subject to adjust the headset and re-image the left and/or right ear.

In another implementation, the test system may process the images of the left and right error and highlight, circle, or otherwise distinguish problem areas associated with the placement of the calibrated headset. For example, if the test system identifies the test subject's ear canal is or excessive amounts of foam are visible in the image of the left ear after placement of the foam, the test system may cause a semi-transparent image of the headset to appear on the image over the test subject's ear canal, such that the test subject is able to see and thereby correct the placement of the headset.

In some cases, the test system may also be equipped with bone conduction devices as part of the calibrated headset which also require accurate placement on the test subject's forehead and cheek to ensure the mechanical vibrations produced are detected by the test subject's internal ear. In some instances, the test system may also request the user to image the forehead and/or cheeks to assist in the placement or alignment of the bone conduction devices.

In some implementations, the test system may be configured to allow the hearing test to begin only during predetermined period of the day or at predefined times of day. For example, it may be known that individuals over the age of 20 are typically more aware or focused during the morning hours of 9 am and 1 pm, while individuals between the ages of 12 and 20 are typically more aware during the hours of 5 pm and 10 pm. In this example, the test system may require test subjects over the age of 20 to beginning the test between 9 am and 1 pm, while restricting the test time for test subjects between the ages of 12 and 20 to after 5 pm but before 10 pm. In this manner, the test system is able to increase a level of awareness and/or focus before the hearing test is begun.

In other implementations, if the test system determines the test subject is likely to disengage or stop the hearing tests before completed. The test system may be configured to alert the test subject to a level of completeness or a nearness to completion. For example, the test system may notify the test subject that the test subject has completed 75% of the test and if the test subject stops now the test subject may need to retake the entire test. In some particular implementations, the test system may also maintain attention of the test subject by having a virtual doctor output the level of completion, encouragement, or advice during the hearing test.

In some cases, the test system may also present the test subject with a score or points based on the quality of the responses and/or answers to the cognitive test segments and/or the hearing test segments. For example, the correctly answering a question, performing a task, or completing a puzzle may earn the test subject points. In other example, the test subject may earn points or increase in score for consistently responding to the same test tone in the same manner. For instance, the more consistently the test subject responds, the more accurate the test becomes and the high the test subject scores. In some cases, the tests subject may be able to redeem or turn in the points for rewards, such as secret test segments, more challenging conative test segments, music, and/or images. In some cases, the scores may be published and compared with other test subjects. In some cases, each time the test subject responds to a tone correctly, earns points, or increases their score, the test system may output an audio indication (such as twinkle sounds), a visual indication (such as stars), or a tactile response (such as a vibration). In this manner, by allowing the test subject to earn points and/or a score the test system may increase the test subject's interest in the hearing test and thereby improve the overall accuracy of the hearing test.

As described herein, the hearing test segment may include tone tests, speech tests, sound tests, and/or combinations of tone, speech, and sound tests. The hearing test segments may also be related to specific frequency ranges, such as a tone test and a speech test with outputs between 100 hertz and 200 hertz. In other cases, a tone test and a speech test designed to test the same frequency range may be considered two separate hearing test segments. In some implementations, a hearing test segment may include tones selected from more than one frequency range. In other implementations, the different hearing test segments may have tones that are stepped by different changes in decibel level. For example, the tones may in one test segment may be stepped by 10 decibels, while in other segments the tones may be stepped by 5 decibel. In some cases, a step or stepped decibel level may be the number of decibels by which a presented stimulus (e.g., a tone or sound) is changed between outputs. In some implementations, the step size may be as small as a one decibel.

In other implementations, the hearing test segments may include frequency modulated (FM) tones in addition to or in lieu of constant frequency tones. In some particular implementations, the hearing test segments may include a tone pattern to which the test subject would issue a single response (e.g., the pattern replaces a single tone within the hearing test segment). For example, the hearing test segment may include multiple short tones, temporally spaced tones, tones in a catchy pattern or recognizable as a song.

Similarly, the cognitive test segments described herein, may include visual tests presented on a display of a device, additional audio based tests intended to increase the awareness and/or responsiveness of the test subject, and/or a combination thereof. In some examples, the cognitive test segments may include a game or puzzle that requires the test subject to perform mental tasks at various difficulty levels. For instance, the test subject may be asked to match a color pattern output on the display of the device and/or to arrange shapes in order to form a larger picture. In other instances, the cognitive test segment may be relatively simple such as turning the computing device 102 by 90 degrees or form a vertical position to a horizontal position (or vice versa) before starting the next hearing test segment. In some particular instances, the cognitive test segments may be passive, such as by asking the user to watch a video or be presented with audio, visual, or tactile stimuli that may be known to increase wakefulness and/or arousal.

FIG. 1 illustrates an example hearing test system 100 according to some implementations. In general, the hearing test system 100 includes a computing device 102 and a calibrated headset system 104. In some instances, such as the illustrated example, the computing device 102 may also be in communication with one or more servers 106 hosting cloud-based services, such as a hearing test monitoring service via, one or more networks 108.

The computing device 102 may be a desktop computer, tablet computer, electronic book reader device, household appliance, cellular phone, smart phone, wearable devices, or other types of devices configured to output audio. In some cases, the computing device 102 may include a display 110 for presenting visual information to the test subject and/or actuators such as vibrating motors, and/or sensors such as accelerometers, in addition to the audio associated with the hearing test segments. For example, the display 110 may be utilize to present the images associated with the left and right ear to the test subject to aid in the placement of the headset 104. In some cases, the display 110 may be utilized in conjunction with an input device for receiving user responses to various test segments. In another example, the display 110 may act as an input device to receive user responses when a tone or part of speech is heard. In some examples, one or more of the actuators may be used to regain user attention to tasks at hand (for instance, via a small vibration or pressure applied to the hand of the test subject).

In other examples, one or more sensors may be used to detect user performance of certain cognitive tests.

The calibrated headset system 104 may also include a left speaker 112 and right speaker 114 for outputting the test tones, parts of speech, and other audio related to the hearing test. In some particular implementations, the calibrated headset system 104 may also include a bone conduction device 116. While the bone conduction device 116 is illustrated as a single transducer located on the forehead it should be understood that the bone conduction device 116 may include multiple transducers for placement at various locations on the test subject's head. For instance, the bone conduction device 116 may be one or more transducers placed or positioned on the temple and at least one cheek to convert sound signals into mechanical vibrations that may be detected by the test subject's internal ear.

In some particular implementations, the computing device 102 may be communicatively coupled to the networks 108 via wired technologies (e.g., wires, USB, fiber optic cable, etc.), wireless technologies (e.g., Wifi, RF, cellular, satellite, Bluetooth, etc.), or other connection technologies. The network 108 is representative of any type of communication network, including data and/or voice network, and may be implemented using a wired infrastructure (e.g., cable, CAT5, fiber optic cable, etc.), a wireless infrastructure (e.g., Wifi, RF, cellular, microwave, satellite, Bluetooth®, etc.), and/or other connection technologies. The network 108 carries data between the servers 106 and the device 102. In some implementations, the device 102 may be connected to the network 108 via a gateway, router, or other type of master device, which facilitates communication between the device 102 and the network 108.

The servers 106 may host any number of cloud services that generally refer to a network accessible platform implemented as a computing infrastructure of processors, storage, software, data access, and so forth that is maintained and accessible via a network such as the Internet. The cloud services do not require end-user knowledge of the physical location and configuration of the system that delivers the services. Common expressions associated with cloud services include "on-demand computing," "software as a service (SaaS)," "platform computing," "network accessible platform" and so forth. In some examples, the cloud-services may include a test monitoring service that allows a hearing health professional to engage with and/or supervise the hearing tests being conducted by the computing device 102. In other examples, the cloud-services may include applications or platforms for collecting hearing related data, updating the software or firmware related to the hearing test on the device 102, recommending hearing aid based on test results, among other types of services.

In one example, a test subject may begin the hearing test process by receiving the calibrated headset system 104 (and various other items, such as the sound damping foam) in the mail and downloading hearing test software onto the computing device 102 from the servers 106. The test subject may then begin the hearing test by initiating the pre-test set up process using the computing device 102. For example, the test subject may launch the hearing tests application and select an option to start a new hearing test or the pre-test set up process. In response, the computing device 102 may present instructions on the display 110 for the test subject to locate the sound damping foam tip of the earphones and to provide an "I am ready" input to the computing device before releasing the foam from a compressing finger grip.

When the ready input is received, the computing device 102 may start a timer. The timer may be associated with a period of time that the sound damping foam may be released from a compressive finger force. The test subject may then provide a second user input indicative of a completion of the insertion. If the foam was inserted before the period of time elapsed, the computing device 102 may display instructions to begin the next set of the setup process, described below. If, however, the timer exceeds the period of time, the computing device 102 may output a sound or present a message on the display 102 instructing the test subject to begin the process of inserting the foam into the ear canal again. In some examples, the computing device 102 may provide instructions and a timer period associated with placing foam in the left ear and a separate set of instructions and timer period associated with placing the foam in the right ear. In some cases, the computing device 102 may be configured to generate a warning or alert to the test subject indicting the remaining time for placing the foam as the period of time elapses.

Once sound damping foam has been acceptably placed in both the left and right ears, the computing device 102 may be configured to output sounds, such as a melody, tones, series of tones, songs, parts of speech, or other audio noise or environmental noise, within the frequency ranges the sound damping foam is intended to block. In some examples, these sounds may be played via built-in speakers of the computing device 102 rather than through the earphones. For instance, the earphones may be disconnected from the computing device 102 to when the sounds are output by the computing device 102. The computing device 102 may request the test subject to provide feedback on whether or not the test subject was able to hear the sounds. If the test subject indicates that he or she heard the sounds then the computing device 102 may instruct the test subject to remove the foam and start over. If, however, the test subject indicates that he or she did not hear the sounds then the computing device 102 may display instructions to utilize an imaging device of the computing device 102 (e.g., a camera on a smart phone) to capture images of the placement of the sound damping foam in each ear.

In the above discussion, the insertion process is described with respect to the sound damping foam. However, in some cases, the foam is attached or coupled to a headset and positioned as single piece. Additionally, in some cases, the headphone may be an in-the-ear earphones, a headband device, a headset with ear cups or covers that fully cover the test subject's ear. Thus, in some implementations, the test subject may place the headset and provide a photo of the test subject's head to ensure the headband, bone conduction devices, or ear cups are correctly aligned. In some particular implementations, the headset may include one or more markers the computing device 102 may utilize to identify a correctly placed or aligned headset. For example, a marker that should be aligned with a center of the test subject's forehead.

The computing device 102 may be configured to present the images of the test subject ears including the foam together with one or more images of correctly placed foam. For example, the computing device 100 may present a fixed image of the test subject's right ear with the foam in place and cycle through a predefined number of images of other individuals with acceptable foam placements. In some examples, the image of other individuals may include additional markings showing why in each case the foam was placed in an acceptable manner. The computing device 100 may then prompt the test subject to confirm via a user input that the test subject's foam has been placed within acceptable margins.

In other implementations, the computing device 100 may analyze or process the images of the right and left ear to determine if the sound damping foam has been acceptably placed. For example, the test system may utilize one or more image processing techniques, such as color matching, blob analysis, signal processing, edge detection, scaling, filtering, among others. In some cases, the computing device 100 may determine the test subject has unacceptably placed the sound damping foam based on the image of the left and/or right ear. The computing device 100 may then re-instruct the test subject on the proper placement and cause the test subject to adjust the foam and re-image the left and/or right ear until the computing device determines the placement is within an acceptable range.

In some examples, the foam is part of or connected to the speaker of an in-ear earphone. In these examples, once the foam and speaker are correctly placed the test subject may begin the hearing test. In other examples, once the computing device determines the foam is correctly placed, the computing device 102 may instruct the test subject to place the calibrated headset system 104 on the test subject's head. In still other examples, the headset system 104 may not include sound damping foam but rather use ear cups or covers to block predefined decibel levels. In this example, once the ear cups or covers are placed correctly the test subject may begin the hearing test. In some case, the computing device 102 may display instructions or instructional videos showing how each component (e.g., the left and right speakers 112 and 114 and the bone conduction device 116) should be placed upon the head. The computing device 102 may repeat the imaging and placement process described above with respect to the foam to ensure the correct placement of the left speaker 112, the right speaker 114, and the bone conduction device 116.

Once the calibrated headset system 104 and/or the foam is adequately placed or positioned on the test subject's head, the computing device 102 may begin the hearing test. In some implementations, the computing device 100 may be configured to alternate or otherwise interleave (e.g., two hearing test segments followed by one cognitive test segments, a hearing test segment followed by two cognitive test segments, etc.) hearing tests segments with one or more cognitive or awareness based test segments. For example, the computing device 102 may cause the calibrated headset system 104 to generate a predetermined number of tones or parts of speech and collect user inputs in response. Once a predetermined number of tones or parts of speech have been output, the computing device 102 may initiate a cognitive test segment, such as color matching on the display 110, moving a slider position on the screen, arrange puzzle pieces to form an image on the display 110, drawing lines on the display 110, reacting to stimulus such as dots or colors presented on the display 110 or a vibration output by a haptic interface, selecting answers related to historical, mathematical, geographical, or other types of trivia questions, among others. By interleaving cognitive test segments into the hearing test segments, the awareness of the test subject may be evaluated and/or increased and the results become more accurate and/or may be better assessed.

In some instances, the computing device 102 may also gauge an initial awareness, wakefulness, focus, or engagement level by asking the test subject if the test subject is a morning person or a night owl and then comparing the answers to a time of day. In other instances, the computing device 102 may gauge the awareness or engagement level based on a tests subject's age, socioeconomic background, level of background noise detected within the environment, among others. In some cases, the computing device 102 may ask the test subject to rate a level of wakefulness or take a wakefulness test as part of one or more of the cognitive test segments.

In some implementations, the computing device 100 may be configured to repeat hearing test segments when the test subject appears to be less than properly engaged. For instance, the computing device 100 may be configured to identify, based on the test results of either the hearing test segments or the cognitive test segment either preceding or following specific hearing test segments, whether the test subject was fully engaged and the test results are accurate. In another instance, the test system may determine that the test subject's clicks or response were at a particular cadence or repetitiveness indicating the test subject was not adequately engaged, or as could possibly be indicated by inconsistent responses to identical tone volumes, or by incorrect responses and/or performance of the cognitive tests, or by self-reported (by the test subject) scores of attentiveness/wakefulness, or by detecting affirmative test-subject responses to fake tones (i.e. it says it's playing a tone but nothing is played).

In some particular situations, the computing device 102 may require the test subject to retake the entire hearing test, when the computing device 102 determines the test subject was not aware or engaged during a threshold portion of the tests or that the test subject's awareness level of engagement level was below a threshold level for a predetermined portion of the hearing test. For instance, if the tests subject fails 75% of the cognitive test segments, the computing device 102 may cause the test subject to retake the entire hearing test.

In these instances, the computing device 102 may repeat the particular hearing tests segment either immediately or at a later time. In some implementations, the computing device 102 may be configured to re-test a first predetermined number of test segments or tones and compare the results to previously collected results to ensure the test subject has regained sufficient awareness. In some particular implementations, the computing device 102 may be configured to compare results of repeated hearing test segments and/or cognitive test segments to determine if the test subject is engaged but producing results indicative of a distracted test taker. In this manner, the computing device 102 is able to eliminate false positives or false negatives.

In some implementations, once the hearing test is complete the computing device 102 may also utilize the demographic information related to the test subject to adjust the results of the hearing test. For example, the a test error margin may be determined based on the demographic information, such as individuals over 65, female, that live in Nebraska typically experience a three decibel level error rate when utilizing the hearing test system 100. In this example, the computing device 102 may adjust the individuals hearing test results by 3 or less decibels to adjust at least partially for the associated error rate.

Figure 2:
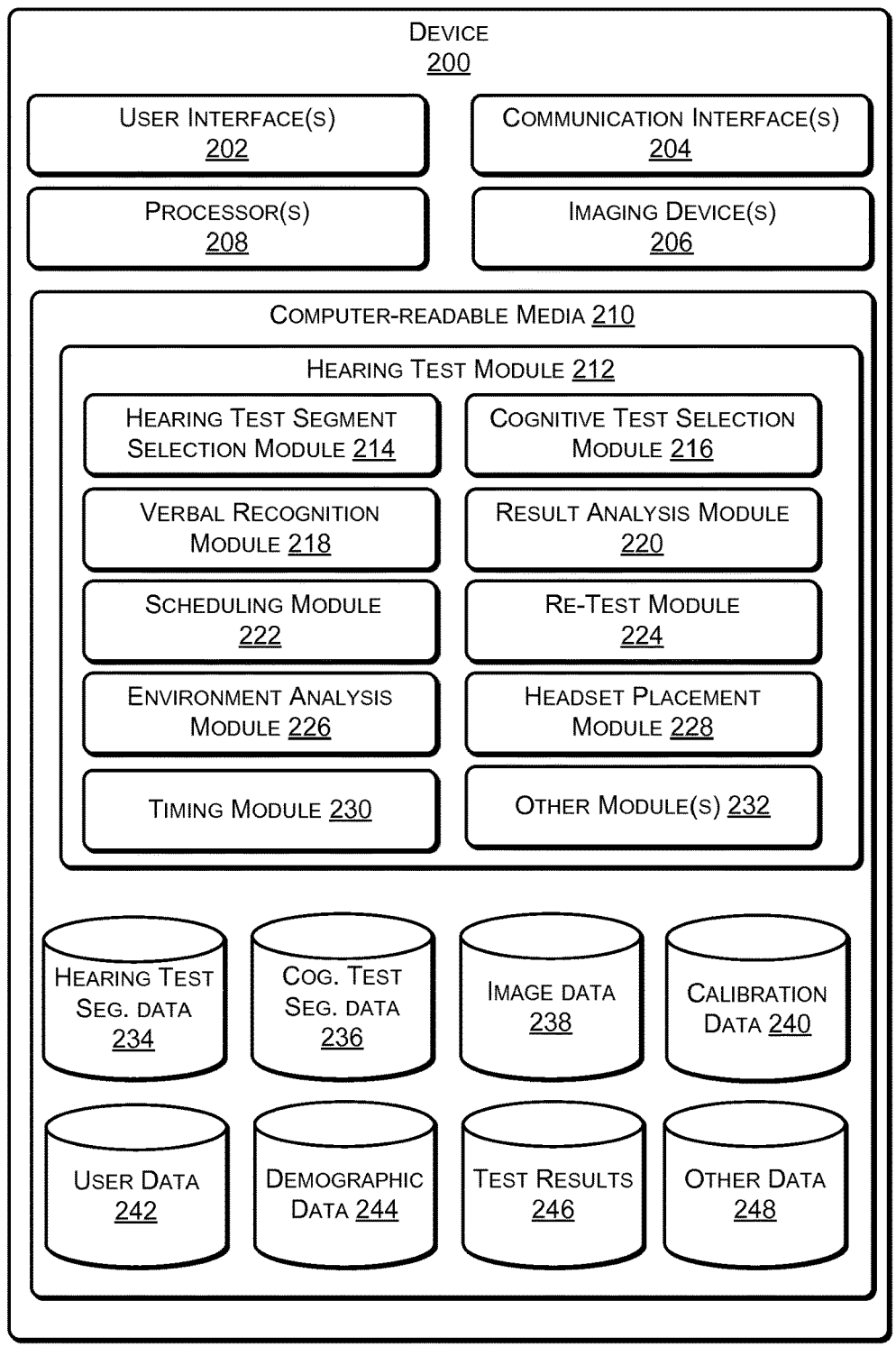
FIG. 2 illustrates an example architecture of a device configured to conduct a hearing test according to some implementations.

FIG. 2 illustrates an example architecture of a device 200 configured to conduct a hearing test according to some implementations. Generally, the device 200 may be implemented as any type of electronic device. For example, the device 200 may include electronic devices, computing devices, desktop computers, tablet computers, notebook computers, cellular or smart phones, etc.

The device 200, generally, includes one or more user interfaces 202 for presenting information or data and for receiving user inputs. The user interfaces 202 may include one or more output components, such as a display or touch screen, and one or more input components, such as keyboards, keypads, joysticks, a mouse, a touch screen, touch pad, drawing pad, sensors, or control buttons, as well as one or more output components, such as a display, and actuators (e.g. vibrating motors). In some implementations, the output components and input components are combined in a single user interface 202 capable of presenting information or data and receiving user inputs. In some particular implementations, the user interfaces 202 may include image processing components and/or audio processing components for receiving gestural inputs and verbal/audio inputs.

The device 200 also includes one or more communication interfaces 204 to facilitate communication between one or more networks (such as the Internet® or one or more local area networks), directly with one or more devices, and/or with one or more cloud services (such as a cloud-based test monitoring service). The communication interfaces 204 may also facilitate communication between one or more wireless access points, a master device, and/or one or more other computing devices as part of an ad-hoc or home network system. The communication interfaces 204 may support both wired and wireless connection to various networks, such as cellular networks, radio, WiFi networks, short-range or near-field networks (e.g., Bluetooth®), infrared signals, local area networks, wide area networks, the Internet®, and so forth.

In some examples, the device 200 also includes or is equipped with one or more imaging devices 206. For example, the device 200 may have one or more cameras for taking photographs and/or video components for capturing image data from the environment. The device 200 includes or accesses components such as at least one or more control logic circuits, central processing units, or processors 208, and one or more computer-readable media 210 to perform the functions of the device 200. Additionally, each of the processors 208 may itself comprise one or more processors or processing cores.

Depending on the configuration of the device 200, the computer-readable media 210 may be an example of tangible non-transitory computer storage media and may include volatile and nonvolatile memory and/or removable and non-removable media implemented in any type of technology for storage of information such as computer-readable instructions or modules, data structures, program modules or other data. Such computer-readable media may include, but is not limited to, RAM, ROM, EEPROM, flash memory or other computer-readable media technology, CD-ROM, digital versatile disks (DVD) or other optical storage, magnetic cassettes, magnetic tape, solid state storage, magnetic disk storage, RAID storage systems, storage arrays, network attached storage, storage area networks, cloud storage, or any other medium that can be used to store information and which can be accessed by the processors 208.

Several modules include instructions, data stores, and so forth may be stored within the computer-readable media 210 and configured to execute on the processors 208. For instance, the hearing test module 512 may be stored and configured to conduct hearing tests and/or evaluations and provide test subjects with the hearing tests results and/or audiograms. In the illustrated example, the hearing test module 212 may include multiple other modules such as a hearing test segment selection module 214, a cognitive test selection module 216, a verbal recognition module 218, a result analysis module 220, a scheduling module 222, a re-test module 224, an environment analysis module 226, a headset placement module 228, a timing module 230, as well as any number of other modules 232. In some cases, some of the modules 214-232 may be combined into a single module or the functionality of each module may be distributed between two or more modules.

The computer-readable media 210 may also store data and/or information usable by the hearing test module 212. For instance, in the illustrated example, the computer-readable media 210 may store hearing test segment data 234 and cognitive test segment data 236 that may be utilized by the hearing test segment selection module 214 and/or the cognitive test segment selection module 216 to generate hearing test segments and cognitive test segments as a hearing test is conducted. In other cases, the hearing test segment data 234 and the cognitive test segment data 236 may be predefined test segments that may selected by the hearing test segment selection module 214 and/or the cognitive test segment selection module 216 during a hearing test.

The computer-readable media 210 may also store image data 238 captured by the image device 206 and accessible to the headset placement module 228 for assisting the headset placement module 228 in determining if the sound damping foam and/or the calibrated headset has been properly positioned on the test subject's head. In some cases, the computer-readable media 210 stores calibration data 240 associated with the calibrated headset system to assist the hearing test module 212 in causing the calibrated headset system to output tones, parts of speech, and other noise at the desired frequency and decibel levels.

In some implementations, the computer-readable media 210 may also store user data 242 and demographic data 244. For example, the user data 242 may include information such as age, sex, race, past hearing test results, other known medical condition, address, former addresses, occupation, and other data related to the test subject and the demographic data 244 may include data or trends known about individuals within certain age groups, sexes, races, occupations, locations (e.g., trends related to hearing loss in different states or countries), and other data relevant to evaluating the hearing of the test subject.

In some cases, the scheduling module 222 may order the hearing test segments and the cognitive test segments selected or generated by the hearing test segment selection module 214 and/or the cognitive test segment selection module 216 based in part on the user data 242 and/or the demographic data 244. For instance, the scheduling module 222 may know the test subject age based on the user data 242 and that the user is in an age range that typically has hearing loss between 4 kilohertz (kHz) based on comparing the test subject's age to the demographic data 244. In this instance, scheduling module 222 may place the hearing test segments associated with the frequency band 4 kHz last in the hearing test so that the test subject has time to adjust to the hearing test before being introduced to tones that may be difficult to identify. In this manner, the scheduling module 222 may improve the accuracy related to hearing test segments associated with frequency ranges in which the test subject is likely to have hearing loss.

The computer-readable media 210 may also store test results 246. For instance, in one example, the re-test module 224 may determine the awareness or engagement of the test subject based in part on comparing the test subjects test results 246 to the user data 242 or the demographic data 244 and thereby determine whether or not to have the test subject re-take particular hearing test segments. In some implementations, the results analysis module 220 may utilize the test results to generate an audiogram that may be utilized to program a hearing aid by a hearing health professional.

In some cases, the environment analysis module 226 may be configured to cause the device 200 to sample the noise in the surrounding environment to determine if the environment is suitable for conducting a hearing test. The verbal recognition module 218 may be configured to process verbal responses provided by the test subject during the hearing test or during cognitive tests. For instance, if the hearing test segment includes outputting a phrase and asking the test subject to repeat the phrase. In this instance, the verbal recognition module 218 may be configured to analyze the phrase as spoken by the test subject to determine if the test subject understood the phrase as output by the calibrated headset system.

In one example, the test subject may begin the hearing test process by receiving a calibrated headset system in the mail and downloading hearing test software onto the device 200. The test subject may begin the hearing test by initiating the pre-test set up process via the user interface 202. For example, the test subject may launch the hearing tests application and select an option to start a new hearing test or the pre-test set up process.

In some implementations, the pre-test set up process begins by the environment analysis module 226 sampling the sound of the surrounding environment. For example, the user interface 202 may include one or more microphones for capturing sounds, such as speech. In other examples, the calibrated headset system may be configured with one or more microphones for capturing sound from an environment. The environment analysis module 226 analyzes the captured sound to determine if the environment is suitable (e.g., the ambient noise is below one or more predefined sound thresholds). If the environmental is not suitable, the device 200 may provide instructions to the test subject via the user interface 202 to select another location and begin the hearing test again.

If, however, a suitable environment is identified by the environment analysis module 226, the device 200 may present instructions on the display for the test subject to locate the sound damping foam and to provide a ready input at the user interface 202 before compressing the foam (e.g., a manual compression may be used) prior to placement of the headset in the ear canal (e.g., in-the-ear earphones). When the ready input is received, the timing module 230 may start a timer. The timer may be associated with a period of time that the sound damping foam associated with the earphones requires before completely decompressing. For instance, the test subject may select the ready input at the user interface 202, open the packaging around the foam, compress the foam (for example, by applying a pressure to both side of the foam), and place the foam and headset. The test subject may provide a second input at the user interface 202 indicative of a completion of the insertion. If the timing module 230 determines the foam was inserted before the period of time elapsed, the device 202 may display instructions to begin the next step of the setup process, described below. If however, timing module 230 determines the test subject exceeded the period of time, the device 200 may output a sound or present a message on the user interface 202 instructing the test subject to begin the process of inserting the foam into the ear canal again.

In some examples, the device 200 may utilize instructions and the time periods for placing the foam in the left ear and that are separate from the instructions and time periods for placing the foam in the right ear. In some cases, the timer module 230 may cause the device 200 to generate a warning or alert to the test subject indicting the remaining time for placing the foam as the period of time elapses. For example, presenting a clock on the user interface 202 that counts down to zero.

Once sound damping foam and/or headset has been acceptably placed in both the left and right ears, the headset placement module 228 may be configured to cause the device 200 to output sounds via a built in-speaker (e.g., a speaker other than a speaker associated with the headset), such as a melody, tones, series of tones, songs, parts of speech, or other audio noise or environmental noise, within the frequency ranges and sound volumes that the sound damping foam is intended to block. The headset placement module 228 may request the test subject to provide feedback via the user interface 202 on whether or not the test subject was able to hear the sounds. If the test subject indicates that he or she did not hear the sounds then the headset placement module 228 may cause the device 200 to instruct the test subject to remove the foam and start over. If, however, the test subject indicates that he or she heard the sounds then the headset placement module 228 may cause the device 200 to display instructions to photograph the test subject's ears via the imaging device 206.

In some cases, the headset placement module 228 may cause the images captured by the test subject to be displayed on one of the user interface 202 in conjunction with one or more images of correctly placed foam and/or headset. For example, the device 200 may present on the user interface 202 a fixed image of the test subject's right ear with the foam and/or headset in place and cycle through a predefined number of images of other individual's right ear with acceptable foam placements. The process may then repeat with the image of the test subjects left ear. In some examples, the image of other individuals may include additional markings showing why in each case the foam was placed in an acceptable manner. In these cases, the device 200 may ask the test subject to confirm via a user interface 202 that the test subject's foam has been placed within acceptable margins.

In other cases, the headset placement module 228 may analyze or process the images of the right and left ear captured by the imaging device 206 to determine if the sound damping foam and/or headset has been acceptably placed. For example, the headset placement module 228 may utilize one or more image processing techniques, such as color matching, blob analysis, signal processing, edge detection, scaling, filtering, among others. In some cases, the headset placement module 228 may determine the test subject has unacceptably placed the sound damping foam and/or the headset based on the image of the left and/or right ear. The headset placement module 228 may cause the device 200 to display instructions on the user interface 202 to cause the test subject to start over with the process of placing the headset.

Once the headset placement module 228 determines the headset is correctly placed, the hearing test may begin. In some cases, the instructions or instructional videos showing how each component (e.g., the left and right speakers and/or the bone conduction device) should be placed upon the head). The headset placement module 228 may repeat the imaging and placement process described above with respect to the foam to ensure the correct placement of the calibrated headset system.

Once the calibrated headset system is adequately placed or positioned on the test subject's head, the hearing test module 212 may begin the hearing test or audiogram. In some implementations, the hearing test segment selection module 214 may select or generate one or more hearing test segments based in part on the hearing test segment data 234, the calibration data 240 associated with the calibrated headset system, the user data 242 known about the test subject, and/or the demographic data 244. Similarly, the cognitive test segment selection module 216 may select or generate one or more cognitive test segments based in part the cognitive test segment data 236, the user data 242 and/or the demographic data 244. For instance, it may be determined based on the data that test subjects between the ages of 30 and 35 respond better to visual cognitive tests, while test subjects between the ages of 55 and 65 respond better to audio based questions.

The scheduler module 222 orders the selected or generated hearing test and the cognitive test segments based in part on the user data 242 and/or the demographic data 244. For example, the scheduling module 222 may be configured to alternate or otherwise interleave (e.g., two hearing test segments followed by one cognitive test segments, a hearing test segment followed by two cognitive test segments, etc.) hearing tests segments with one or more congestive or awareness based test segments. By interleaving cognitive test segments into the hearing test segments, the awareness of the test subject is increased and the results produced by the hearing test module 212 become more accurate.

In some implementations, the re-test module 224 may be configured to analyze the results of each hearing test segment as the hearing test is conducted by the hearing test module 212. If the re-test module 224 determines that the test result 246 of one or more segments appear to indicate that the test subject was not engaged, the re-test module 224 may cause the scheduling module 222 to repeat the particular hearing test segments to ensure the end results are accurate. For instance, the re-test module 224 may be configured to identify based on the test results 246 of either the hearing test segments or the cognitive test segment. For instance, the re-test module 224 may determine the test subject's clicks or responses to a hearing test segment were at a particular cadence or repetitiveness indicating the test subject was not adequately engaged. In some cases, the re-test module 224 may compare the test results 246 to demographic data 244 in order to determine a level of engagement of the test subject. For example, the demographic data 244 may include test results of past test subjects that may be utilized by the re-test module 224 to determine the level of engagement. In some cases, the level of engagement may be measured or evaluated in respect to an age, race, time of day, etc. associated with the test subject and/or the test.

In some cases, the repeated hearing test segment may have tones that are grouped at a closer decibel range (e.g., 5 decibel difference v. 15 decibel difference) than in the original hearing test segment, to attempt to improve the accuracy of the test subject's hearing threshold with respect to the particular frequency levels being tested. In other cases, the decibel range of the tones may narrow as the test system determines that the test subject is in frequency/decibel range in which the test subject is experiencing hearing loss or derogation.

Once each test segment has been approved by the re-test module 224, the results analysis module 220 may utilize the test results to generate a hearing evaluation or an audiogram that may be utilized by a hearing health professional to program a hearing aid. In some cases, the results analysis module 220 may output via the user interface 202 a notice to the test subject that the test subject should seek further evaluation from a hearing health professional or that the test subject may benefit from hearing aids. In some particular instance, the results analysis module 220 may output via the user interface 202 a type of hearing aid and/or a power (for example, low, medium, or high) associated with a hearing aid suitable for correcting the test subject's hearing loss. In other cases, the results analysis module 220 may cause the device 200 to output via the user interface 202 an audiogram showing the test subjects hearing loss, for instance, graphically and/or numerically.

Figure 3:
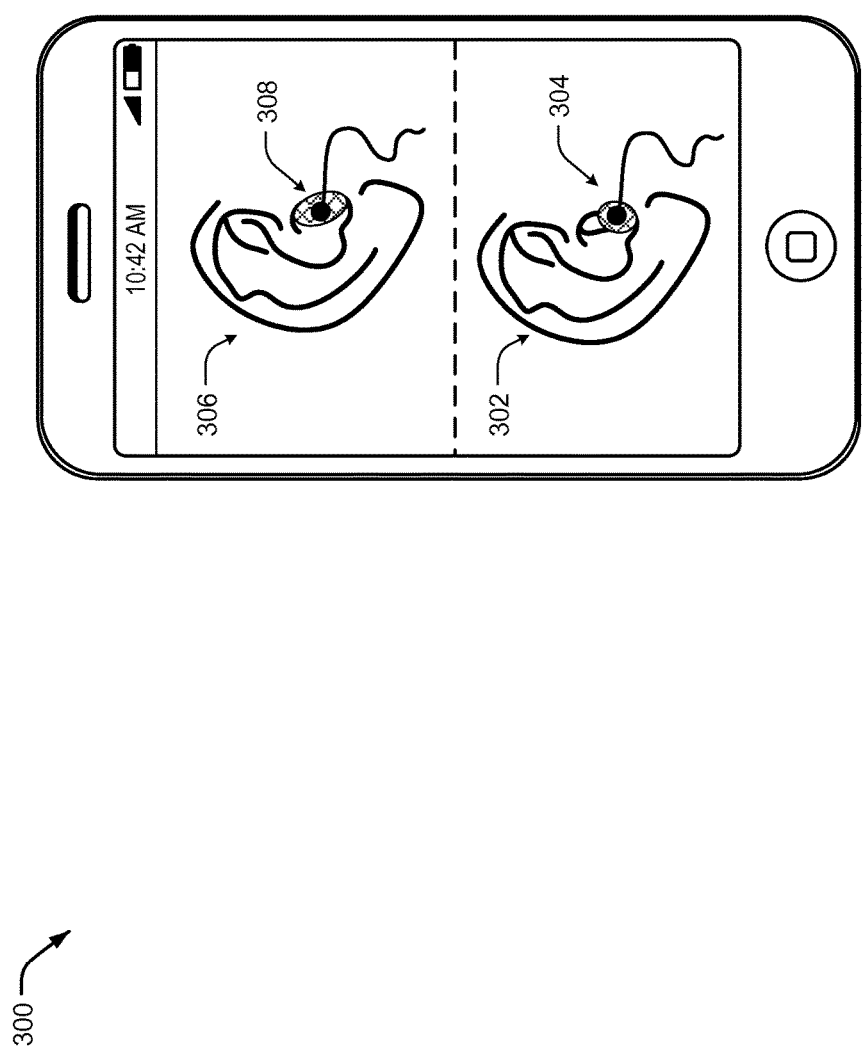
FIG. 3 illustrates an example computing device displaying an image of a test subject's right ear after incorrect placement of sound damping foam together with an image of another individual's right ear with an acceptable placement of the in-the-ear earphone according to some implementations.

FIG. 3 illustrates an example computing device 300 displaying an image 302 of a test subject's right ear after placement of sound damping foam 304 together with an image 306 of another individual's right ear with an acceptable placement of the in-the-ear earphone 308 according to some implementations. For example, one of the issues with test subject driven hearing exams and evaluations is improper placement of the headset and/or the sound damping foam associated with the headset, which allows environmental noise to undermine the accuracy of the hearing test results. Additionally, it should be understood that, in the illustrated example, an earphone actuator connected to the sound damping foam via an earphone cable in an in-the-ear earphone 308. However, in other examples, other types of headsets or earphone may be utilized, such as ear cup or over-the-ear earphone. Additionally, it should be understood that in some cases, the foam may not be visible in the image depending on the type and configuration of the earphones.

In the illustrated example, the test subject may be able to determine that the foam or the in-the-ear earphone 304 have been inadequately placed when compared to the example earphone placement 308, as the foam associated with the example earphone placement 308 completely covers the ear in the image 306, while the foam of the in-the-earphone 304 in the image 302 of the test subject's ear does not cover the ear canal. In some examples, the image 306 may change or cycle through a predefined number of images, such that the test subject is able to compare the image 302 of the test subject's ear to multiple images of another individual's ear to better understand what a proper placement of the in-the-ear earphone 308 looks like.

Figure 4:
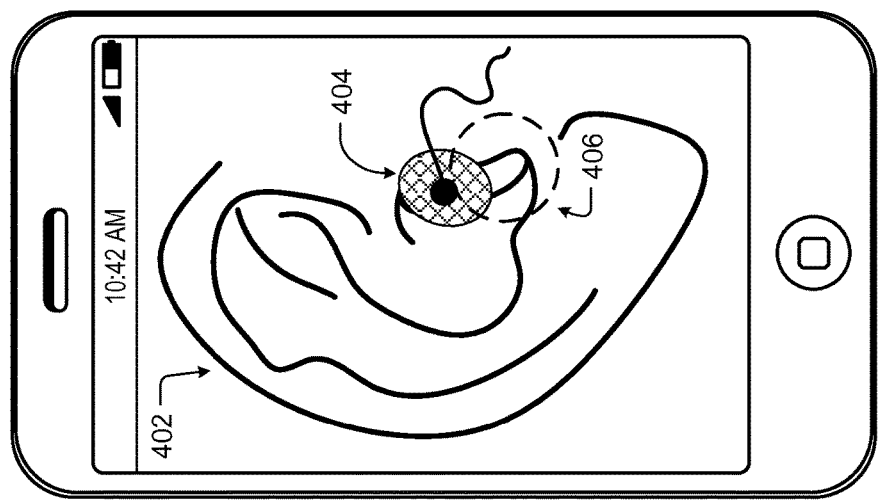
FIG. 4 illustrates an example computing device displaying an image of the test subject's right ear after placement of in-the-ear earphone according to some implementations.

FIG. 4 illustrates an example computing device 400 displaying an image 402 of the test subject's right ear after placement of in-the-ear earphone 404 according to some implementations. For example, as discussed above, one of the issues with test subject driven hearing exams and evaluations is improper placement of the sound damping foam, the headset or the earphones, which allows environmental noise to undermine the accuracy of the hearing test results. Additionally, it should be understood that, in the illustrated example, an earphone actuator connected to the sound damping foam via an earphone cable in an in-the-ear earphone 404. However, in other examples, other types of headsets or earphones may be utilized, such as an ear cup or over-the-ear earphone. Additionally, it should be understood that in some cases, the foam may not be visible in the image depending on the type and configuration of the earphones.

In the illustrated example, the hearing test module operating on the computing device 400 may determine the foam or the in-the-ear earphone 404 has been inadequately or improperly placed by analyzing the image 402 and identifying that the ear canal is visible in the image 402. In this example, the hearing test module may insert an indication 406 of the improper placement into the image 402 and cause the computing device 400 to display the image 402 including the indication 406 to the test subject. In this manner, the test subject may view the image 402 and the indication 406 and, thereby, determine how to improve the placement or adjust the placement of the in-the-ear earphones 404 to improve the results of the hearing test.

FIGS. 5-8 are flow diagrams illustrating example processes for implementing a test subject driven hearing test. The processes are illustrated as a collection of blocks in a logical flow diagram, which represent a sequence of operations, some or all of which can be implemented in hardware, software or a combination thereof. In the context of software, the blocks represent computer-executable instructions stored on one or more computer-readable media that, which when executed by one or more processors, perform the recited operations. Generally, computer-executable instructions include routines, programs, objects, components, data structures and the like that perform particular functions or implement particular abstract data types.

The order in which the operations are described should not be construed as a limitation. Any number of the described blocks can be combined in any order and/or in parallel to implement the process, or alternative processes, and not all of the blocks need be executed. For discussion purposes, the processes herein are described with reference to the frameworks, architectures and environments described in the examples herein, although the processes may be implemented in a wide variety of other frameworks, architectures or environments.

Figure 5:
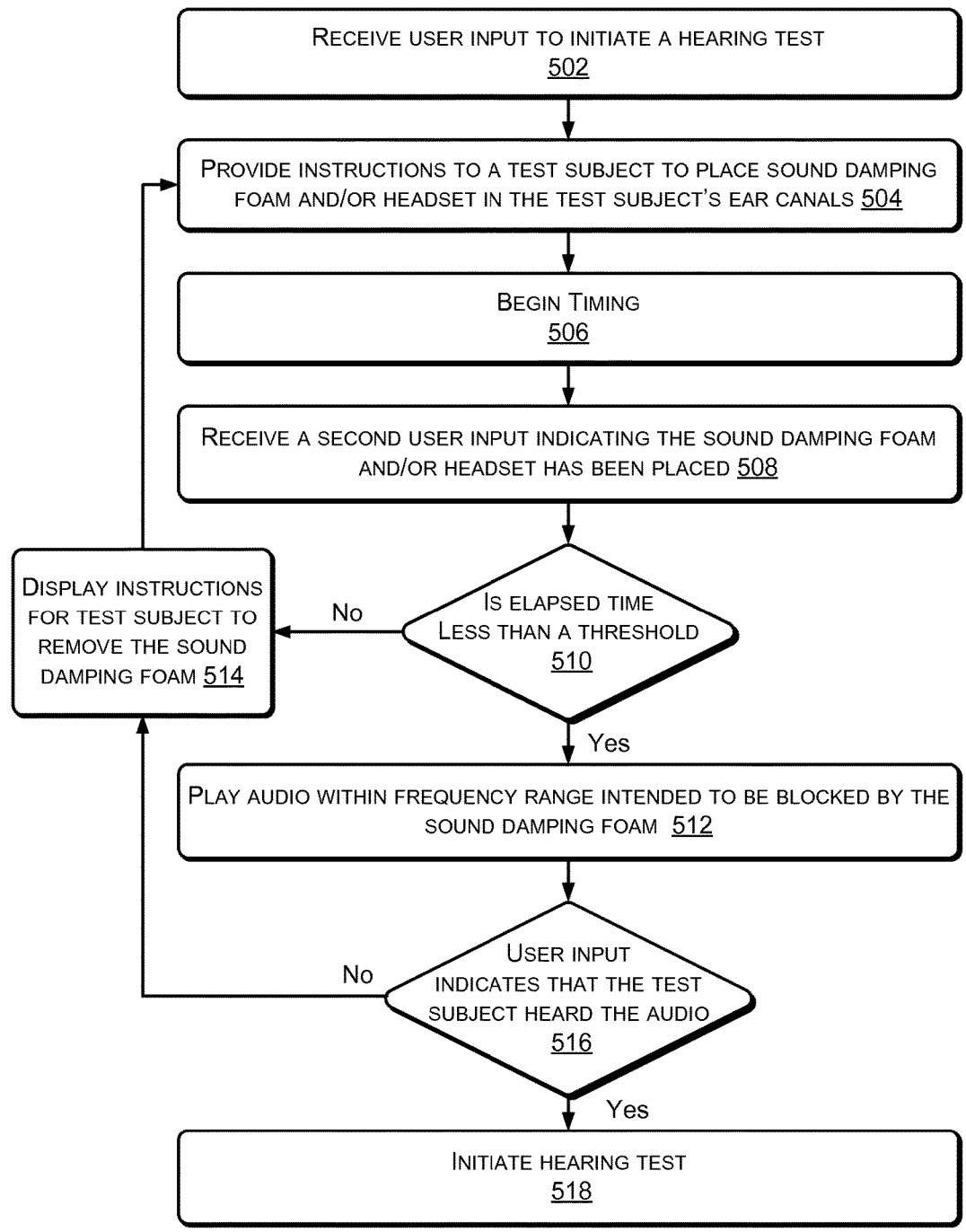
FIG. 5 is an example flow diagram showing an illustrative process associated with a pre-test setup according to some implementations.

FIG. 5 is an example flow diagram showing an illustrative process 500 associated with a pre-test setup according to some implementations. As described above, one cause of inaccurate test results with regards to at home hearing tests or evaluations, is incorrect placement of sound damping foam intended to block or prevent the test subject from hearing select frequencies. In some implementations described herein, placement of sound damping foam may be improved and thereby the accuracy of the hearing test may also be improved.

For example, at 502, a hearing test module, such as hearing test module 212 of FIG. 2, operating on a device, such as devices 102, 200, 300, and 400 of FIGS. 1-4, may receive a user input to initiate a hearing test.

At 504, the hearing test module may provide instruction to a test subject to place sound damping foam and/or headset in the test subject's ear canals. For example, the hearing test module may display the instructions on one or more displays associated with the device. In other examples, the hearing test module may cause the device to output audio instructions via one or more speakers associated with the device. For instance, the test subject may be instructed to select a ready input at a user interface, open the packaging around the foam, and place the foam within each of the test subject's ear canals.

At 506, the hearing test module begins a timer associated with monitoring a length of time it take the test subject to insert or place the foam within the test subject's ear canals. In some implementations, the timer is associated with a period of time the test subject has to place the foam within the ear canals. For example, the timer may be associated with a period of time that the sound damping foam take to return to a fully decompressed state after having been compressed (e.g., a period in the range of ten seconds after manual compression). Thus, providing the foam time to expand within the ear canals once the earphones of the headset are placed.

At 508, the hearing test module receives a second user input from the test subject. The second user input indicates the sound damping foam and/or headset has been placed. At 510, the hearing test module determines if the elapsed time is less than a threshold (e.g., the period of time allocated to place the sound damping foam). For example, if the foam was inserted before the period of time elapsed, the process 500 may proceed to 512. If, however, the test subject exceeded the period of time, the process 500 may proceed to 514 and display inductions for the test subject to remove the sound damping foam. The process 500 may then return to 504.

In some cases, the hearing test module may be configured to provide a visual or audio indication of the time remaining before the period elapses. In other cases, the process 500 may not wait for the second user input but proceed to 514 when the timer exceeds the threshold. In these cases, the hearing test module may cause the device to alert the test subject that the time period has elapsed prior to proceeding to 514.

At 512, the hearing test module may play or output audio or other noises within a frequency range intended to be blocked by the sound damping foam (e.g., below 50 db). For example, the hearing test module may cause the device to play or output sounds via a built-in speaker system, such as a melody, tones, series of tones, songs, parts of speech, or other audio noise or environmental noise, within the frequency ranges the sound damping foam is intended to block.

At 516, the hearing test module determines if the user input indicates that the test subject heard the audio. For example, the audio may include a sentence or phrase that the test subject is supposed to repeat. In other cases, the user input may be a selection of an option or button on the device. If the user input indicates the test subject heard the audio, then the process moves back to 514. Otherwise, the process 500 advances to 518 and the device may initiate the hearing tests or perform additional pretest setup processes.

Figure 6:
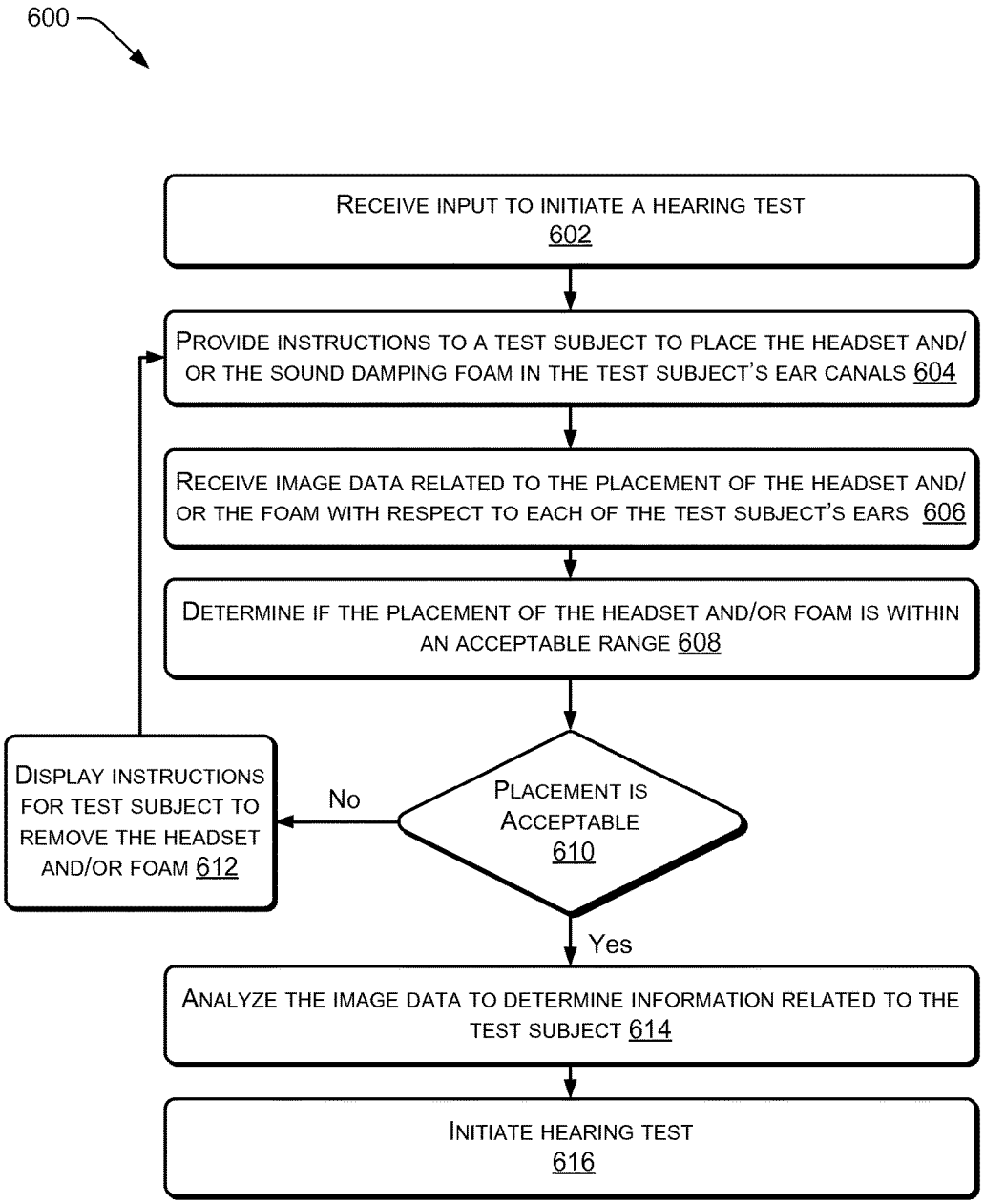
FIG. 6 is another example flow diagram showing an illustrative process associated with a pre-test setup according to some implementations.

FIG. 6 is an example flow diagram showing an illustrative process 600 associated with a pre-test setup according to some implementations. For example, the process 600 may be an alternative to the process s 500 of FIG. 5. As described above, one cause of inaccurate test results with regards to at home hearing tests or evaluation, is incorrect placement of sound damping foam intended to block or prevent the test subject from hearing select frequencies. In some implementations described herein, placement of sound damping foam may be improved and thereby the accuracy of the hearing test may also be improved.

For example, at 602, a hearing test module, such as hearing test module 212 of FIG. 2, operating on a device, such as devices 102, 200, 300, and 400 of FIGS. 1-4, may receive a user input to initiate a hearing test. For example, the test subject may launch a hearing test application from one or more mobile devices after having received a calibrated headset system in the mail.

At 604, the hearing test module may provide instruction to a test subject to place a headset (such as the calibrated headset system 104 of FIG. 1) and/or sound damping foam in the test subject's ear canals. In other cases, such as when an over-the-ear headset is utilized, the hearing test module may provide instructions to the test subject to place the headset over the test subject's ears. For example, the hearing test module may cause the device to display the instructions on one or more displays associated with the device. In other examples, the hearing test module may cause the device to output audio instructions via one or more speakers associated with the device. For instance, the test subject may be instructed to select a ready input at a user interface, open the packaging around the foam, and place the foam within each of the test subject's ear canals. In another instance, the test subject may be instructed to select a ready input at a user interface, align the left speaker and right speaker with the corresponding ear, and to place the bone conduction devices on the forehead and/or each cheek.

At 606, the hearing test module receives image data related to the placement of the headset and/or the foam with respect to each of the test subject's ears. For example, the device may be equipped with one or more cameras or other imaging technologies that the test subject may utilize to capture the image data. In other cases, the device and the hearing test module operating on the device may receive the image data from another device configured to capture image data.

At 608, the hearing test module determines if the placement of the headset and/or the foam is within an acceptable range. For example, the hearing test module may utilize one or more image processing techniques, such as color matching, blob analysis, signal processing, edge detection, scaling, filtering, among others. In some cases, the hearing test module may attempt to identify if the ear canal is visible in the image data (e.g., not covered by the foam or headset), if the ear is visible in the image data (e.g., not covered by the headset), or if a gap exists between the test subject's head and the headset or foam. In some cases, the hearing test module may determine if for example, the bone conduction device is placed near the center of the test subject's forehead. For example, by determining the number of pixels associated with the test subject's forehead on either side of the bone conduction device.

At 610, if the hearing test module determines that the placement is not acceptable, the process 600 advances to 612. Otherwise, the process 600 proceeds to 614. At 612, the hearing test module causes the device to display instructions of the test subject to remove the headset and/or foam and the process 600 returns to 604.

At 614, the hearing test module may analyze the image data to determine additional information related to the test subject. For example, the hearing test module may determine a relative age, sex, race, other demographic information about the test subject, as well as test data such as time of day, location, environment, etc. In some cases, as described above, the demographic information associated with the test subject may be used to tailor the hearing test and/or to improve the accuracy of the results. In other implementations, rather than analyzing the image data, the hearing test module may collect the demographic information via a short questionnaire presented on the display of the device.

At 616, the hearing test module initiates the hearing test. For example, the hearing test module may begin outputting test tones associated with a hearing test segment. In other cases, the hearing test module may present the test subject with a cognitive test segment to evaluate and/or increase the awareness of the test subject before the test begins. In some instances, the preliminary cognitive test segment may be used as a baseline awareness level for the remainder of the hearing test.

Figure 7:
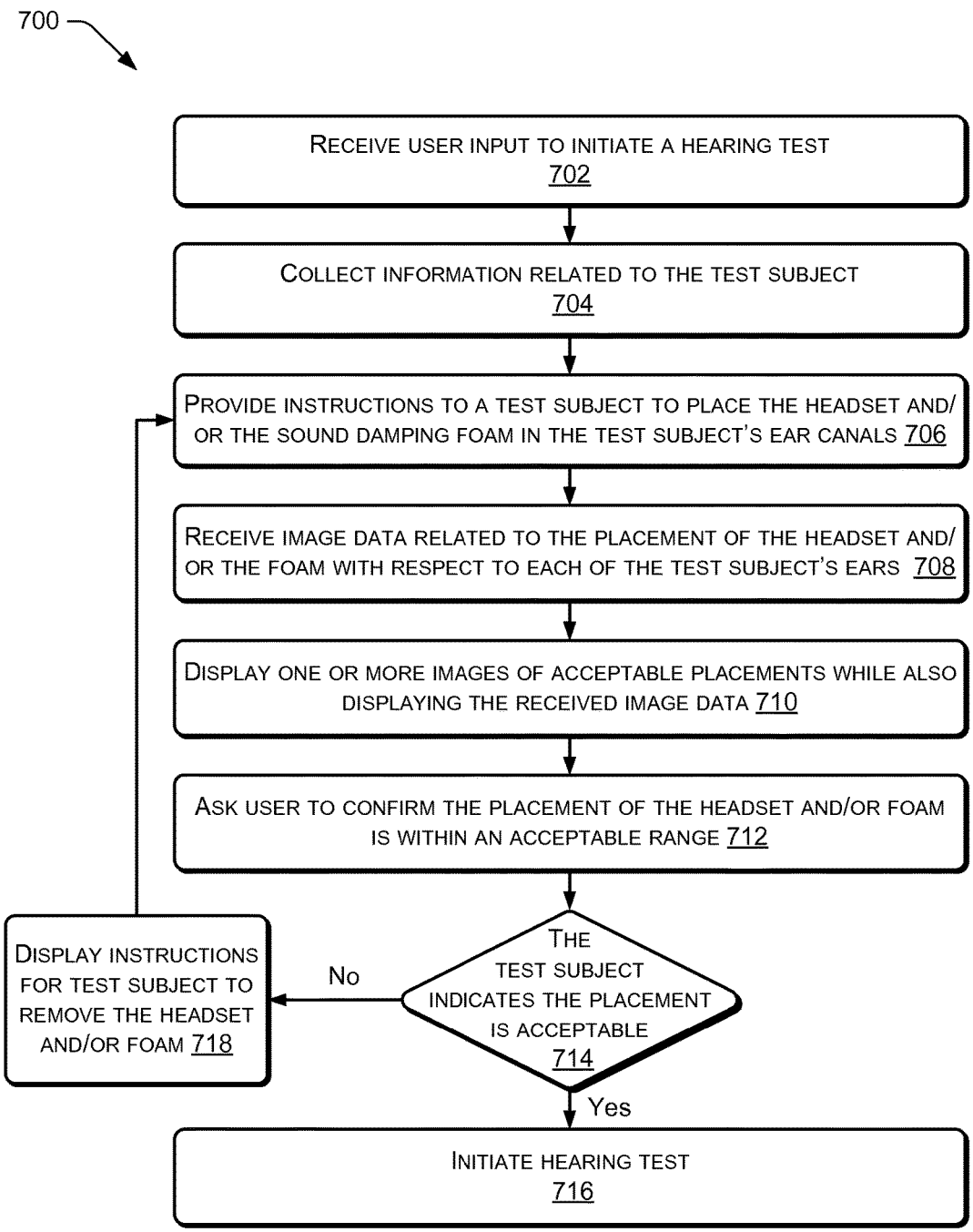
FIG. 7 is another example flow diagram showing an illustrative process associated with a pre-test setup according to some implementations.

FIG. 7 is an example flow diagram showing an illustrative process 700 associated with a pre-test setup according to some implementations. As described above, one cause of inaccurate test results with regards to at home hearing tests or evaluation, is incorrect placement of sound damping foam and/or the headset intended to block or prevent the test subject from hearing select frequencies. In some implementations described herein, placement of sound damping foam may be improved and thereby the accuracy of the hearing test may also be improved.

For example, at 702, a hearing test module, such as hearing test module 212 of FIG. 2, operating on a device, such as devices 102, 200, 300, and 400 of FIGS. 1-4, may receive a user input to initiate a hearing test. For example, the test subject may launch a hearing test application from one or more mobile devices after having received a calibrated headset system in the mail.

At 704, the hearing test module may collect information related to the test subject. For example, the hearing test module may collect data related to an age, a sex, a race, other demographic information about the test subject, and/or time of the test or location of the test before starting the hearing test. In some cases, as described above, the demographic information associated with the test subject may be used to tailor the hearing test and/or to improve the accuracy of the results.

At 706, the hearing test module may provide instruction to a test subject to place a headset (such as the calibrated headset system 104 of FIG. 1) and/or sound damping foam in the test subject's ear canals. In other cases, such as when an over-the-ear headset is utilized, the hearing test module may provide instructions to the test subject to place the headset over the test subject's ears. For example, the hearing test module may cause the device to display the instructions on one or more displays associated with the device. In other examples, the hearing test module may cause the device to output audio instructions via one or more speakers associated with the device. For instance, the test subject may be instructed to select a ready input at a user interface, open the packaging around the foam, and place the foam within each of the test subject's ear canals. In another instance, the test subject may be instructed to select a ready input at a user interface, align the left speaker and right speaker with the corresponding ear, and to place one or more bone conduction devices on the forehead and/or each cheek.

At 708, the hearing test module receives image data related to the placement of the headset and/or the foam with respect to each of the test subject's ears. For example, the device may be equipped with one or more cameras or other imaging technologies that the test subject may utilize to capture the image data. In other cases, the device and the hearing test module operating on the device may receive the image data from another device configured to capture image data.

At 710, the hearing test module causes the device to display one or more images of acceptable placements while also displaying the received image data. For example, the hearing test module may divide the display and present the images of the acceptable placement in one pane and the image data in another. In other cases, the hearing test module may cause the device to display the images of the acceptable placement as semi-transparent images overplayed on the image data.

At 712, the hearing test module prompts the test subject to confirm the placement of the headset and/or foam is within an acceptable range. For example, the hearing test module may cause the device to prompt on the display or the hearing test module may cause the headset system to output the prompt as a sound.

At 714, if the test subject indicates the placement is acceptable, the process 700 proceeds to 716. Otherwise, the process proceeds to 718. At 718, the hearing test module causes the device to display instructions of the test subject to remove the headset and/or foam and the process 700 returns to 706.

At 716, the hearing test module initiates the hearing test. For example, the hearing test module may begin outputting test tones associated with a hearing test segment. In other cases, the hearing test module may present the test subject with a cognitive test segment to evaluate and/or change the awareness of the test subject before the test begins, or during the test. In some instances, the preliminary cognitive test segment may be used as a baseline awareness level for the remainder of the hearing test.

Figure 8:
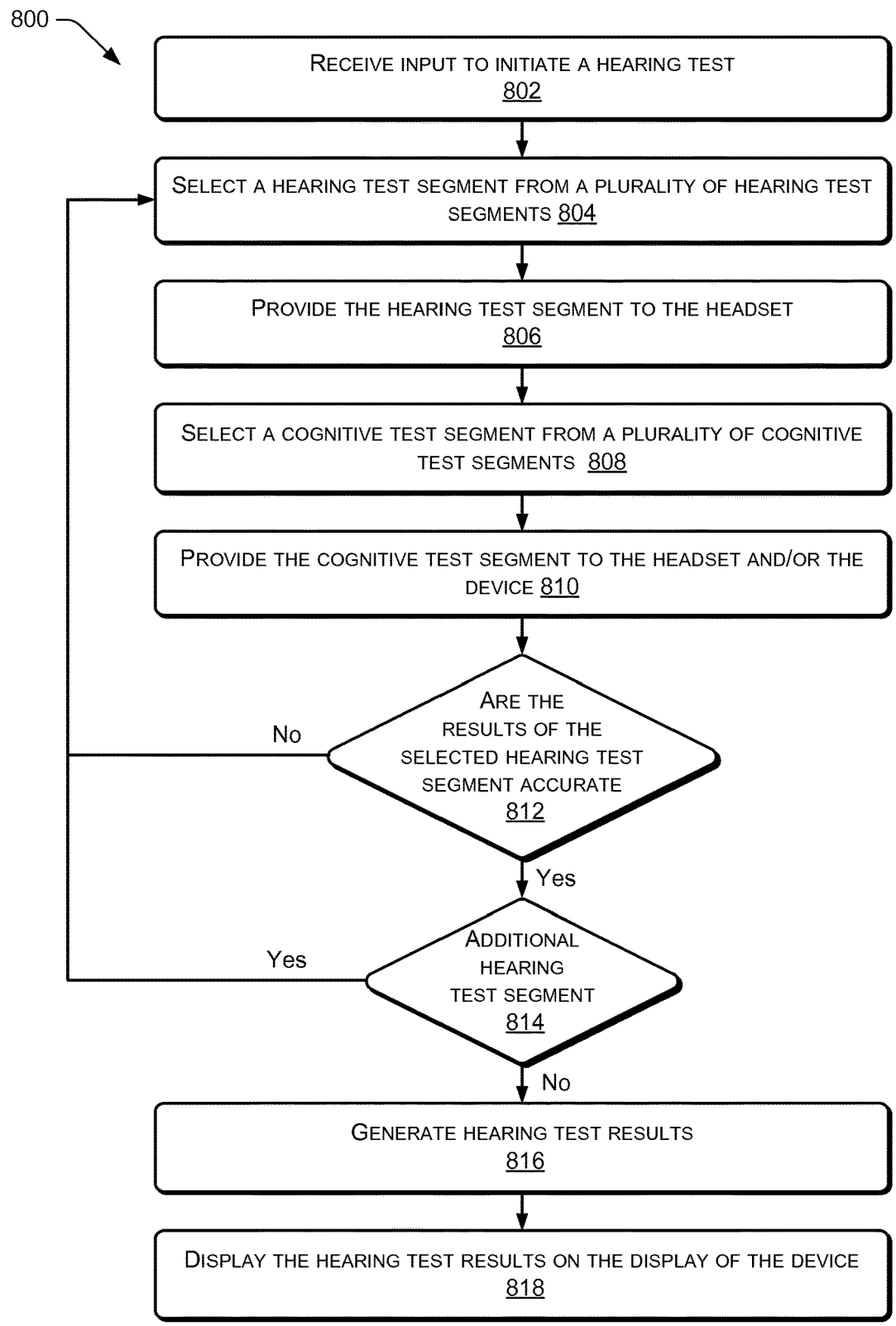
FIG. 8 is an example flow diagram showing an illustrative process associated with conducting a hearing test according to some implementations.

FIG. 8 is an example flow diagram showing an illustrative process 800 associated with conducting a hearing test according to some implementations. As described above, one cause of inaccurate test results with regards to at home hearing tests or evaluations, is a reduction in the awareness or engagement of the test subject as the hearing test progresses, as the hearing test may be both long and tedious. Therefore, described herein are implementations to improve the awareness and/or engagement of a test subject while conducting a hearing test.

At 802, a hearing test module, such as hearing test module 212 of FIG. 2, operating on a device, such as devices 102, 200, 300, and 400 of FIGS. 1-4, may receive a user input to initiate a hearing test. For example, the test subject may launch a hearing test application from one or more mobile devices after having received a calibrated headset system in the mail.

At 804, the hearing test module may select a hearing test segment from a plurality of hearing test segments. In one example, the hearing test module may select a next hearing test segment based on demographic information known about the test subject and/or the larger population. For instance, the hearing test module may select a test segment the test subject is likely to pass based on the occupation of the test subject and typical hearing loss patterns associated with the test subject's occupation.

At 806, the hearing test module provides the selected hearing test segment to the headset for reproduction as sound. For example, the hearing test module may cause the headset to output a series of calibrated tones to which the test subject may respond by interacting with a user interface of the device when the test subject hears one of the tones. In other cases, the hearing test segment may or may not output tones and present a question on the display asking if the test subject heard the tone. In some cases, by asking the test subject if the test subject heard a tone when one was not played, the hearing test module may be able to eliminate false positives or further gauge the awareness of the test subject.

At 808, the hearing test module may select a cognitive test segment from a plurality of cognitive test segments. In one example, the hearing test module may select a next cognitive test segment based on demographic information known about the test subject and/or the larger population. For instance, the hearing test module may select a test segment that is likely to be of interest to the test subject, such as a simple word game or puzzle game that are typically played by the test subject's age group. In other instances, the cognitive test segment may be passive, such as playing lively music, displaying images, or watching a video.

At 810, the hearing test module provides the selected cognitive test segment to either the headset for reproduction as sound or the device for presentation on the display, or output may occur via actuators (e.g. vibrating motors), and input may be acquired via sensors integrated with the mobile device such as a microphone, video camera, accelerometers, touch screen, etc. Feedback could also be delivered to the test subject in 'real time', as inattention is detected, Such feedback could include audio/visual/tactile cues to re-attain the subjects attention. In one example, the cognitive test segment may include outputting sounds at the headset while displaying content on the display of the device to cause the test subject to interact with the display in response to various sounds output by the headset.

At 812, the hearing test module determines if the results of the selected hearing test segment are accurate. For example, the hearing test module may compare the test results to results of other test segments. In another example, the hearing test module may determine if the user inputs were regular or at set intervals, as if the test subject was entering inputs out of habit. In some implementations, the hearing test module may determine that the results of the hearing test are inaccurate based on results of the cognitive test segment. For example, if the test subject scored poorly on the cognitive test segment it may be an indication that the test subject is not engaged and that the hearing test segment should be retested. If the hearing test module determines that the results are accurate the process 800 advances to 814 and the selected hearing test segment is removed from the plurality of hearing test segments. Otherwise, the process 800 returns to 804 and another hearing test segment is selected from a pool of hearing test segments including the hearing test segment with the inaccurate results.

At 814, the hearing test module determines if additional hearing test segments remain to be tested. If there are additional hearing test segments, the process 800 returns to 804 and another hearing test segment is selected. Otherwise, the process 800 proceeds to 816. At 816, the hearing test module generates hearing test results. For example, the hearing test module may generate an audiogram or another visual representation of the test subject's hearing loss. In some cases, the test results may include a message for the test subject to seek further assistance from a hearing health professional. In some implementations, the test data collected during the hearing test may be provided to a remote server or to a device accessible to a hearing health professional. In this implementation, software operating on the remote server or the hearing health professional may generate the audiogram. In some specific implementations, the test results may include a recommendation of a hearing aid and a link to a location from which the hearing aid may be purchased.

At 818, the hearing test module may cause the device to display the hearing test results to the test subject. In some cases, the message displayed may be the audiogram, the other visual representation of the test subject's hearing loss, and/or a message to seek further assistance from a hearing health professional.

Although the subject matter has been described in language specific to structural features, it is to be understood that the subject matter defined in the appended claims is not necessarily limited to the specific features described. Rather, the specific features are disclosed as illustrative forms of implementing the claims.

What is claimed is:

1. A device comprising:
   one or more user interfaces for receiving user input;
   an input interface for releasably coupling to at least one speaker;
   a display;
   one or more processors; and
   non-transitory computer-readable storage media storing computer-executable instructions, which when executed by the one or more processors cause the one or more processors to:
   receive image data associated with an ear of the test subject after sound damping foam has been placed in an ear canal of the ear;
   present on the display, image data associated with an ear of the test subject after sound damping foam has been placed in an ear canal of the ear and at least one image illustrating a correct placement of the sound damping foam within an ear canal;
   provide audio associated with a hearing test segment to the speaker;
   receive user inputs associated with the audio output by the speaker;
   present a cognitive test segment on the display;
   receive user inputs associated with the cognitive test segment;
   determine an awareness level of the test subject based at least in part on the user inputs associated with the cognitive test segment;
   determine the awareness level is above a threshold;
   mark the hearing test segment as complete; and
   display test results on the display.

2. The device as recited in claim 1, wherein the computer-readable storage media further stores computer-executable instructions, which when executed by the one or more processors cause the one or more processors to select the hearing test segment from a plurality of hearing test segments based at least in part on information about the test subject.

3. The device as recited in claim 1, wherein the computer-readable storage media further stores computer-executable instructions, which when executed by the one or more processors cause the one or more processors to select the cognitive test segment from a plurality of cognitive test segments based at least in part on demographic information associated with a plurality of prior test subjects.

4. The device as recited in claim 1, wherein the computer-readable storage media further stores computer-executable instructions, which when executed by the one or more processors cause the one or more processors to determine that each of a plurality of hearing test segments are marked as completed before outputting the test results.

5. The device as recited in claim 1, wherein the hearing test segment includes outputting at the speaker at least one of:
   a test tone;
   a part of speech;
   a phrase;
   a melody;
   a pattern of tones; or
   environmental noises.

6. A device comprising:
   one or more user interfaces for receiving user input;
   an input interface for releasably coupling to at least one speaker;
   a display;
   one or more processors; and
   non-transitory computer-readable storage media storing computer-executable instructions, which when executed by the one or more processors cause the one or more processors to:
   process image data associated with an ear of the test subject after sound damping foam has been placed in an ear canal of the ear to determine that the sound damping foam is inadequately placed;
   present on the display the image data and an indication of a location at which the foam has been inadequately placed or should be placed;
   select a hearing test segment from a plurality of the hearing test segments of a hearing test;

output audio associated with a hearing test segment at a speaker, the speaker associated with the device;

receive user inputs associated with the audio output by the speaker;

select a cognitive test segment from a plurality of the cognitive test segments of the hearing test;

present the cognitive test segment on a display of the computing device;

receive user inputs associated with the cognitive test segment presented on the display from the user interface;

determine an awareness level of a test subject based at least in part on the user inputs associated with the cognitive test segment;

determining that the awareness level of the test subject is below a threshold; and re-outputting, at the speaker, the audio associated with the hearing test segment;

re-present the cognitive test segment on a display of the computing device;

re-receive user inputs associated with the cognitive test segment presented on the display from the user interface;

re-determine an awareness level of the test subject based at least in part on the user inputs associated with the cognitive test segment;

determine that the awareness level is above a threshold;

mark the hearing test segment as complete; and display results of the hearing test on the display.

7. The device as recited in claim 6, wherein the hearing test segment is selected based at least in part on at least one of receive an initialization input from the input interface, the initialization input to initiate the hearing test.

8. The device as recited in claim 6, wherein the cognitive test segment is selected based at least in part on at least one of:
 demographic information related to the test subject;
 a time of day; or
 one or more environmental variables.

9. The device as recited in claim 6, wherein outputting audio associated with the hearing test segment includes causing the speaker to output at least one of:
 a test tone;
 a part of speech;
 a phrase; or
 environmental noises.

10. The device as recited in claim 6, wherein the cognitive test segment includes visual information presented on the display.

11. The device as recited in claim 6, further comprising determining each of the plurality of hearing test segments have been marked as completed before outputting the results of the hearing test.

12. The device as recited in claim 6, further comprising an image device to capture the image data.

13. A device comprising:
 one or more user interfaces for receiving user input;
 an input interface for releasably coupling to at least one speaker;
 a display;
 one or more processors; and
 non-transitory computer-readable storage media storing computer-executable instructions, which when executed by the one or more processors cause the one or more processors to:

receive image data associated with an ear of the test subject after sound damping foam has been placed in an ear canal of the ear;

present on the display, image data associated with an ear of the test subject after sound damping foam has been placed in an ear canal of the ear and at least one image illustrating a correct placement of the sound damping foam within an ear canal;

select a hearing test segment from a plurality of the hearing test segments of a hearing test;

output audio associated with a hearing test segment at a speaker, the speaker associated with the device;

receive user inputs associated with the audio output by the speaker;

select a cognitive test segment from a plurality of the cognitive test segments of the hearing test;

present the cognitive test segment on a display of the computing device;

receive user inputs associated with the cognitive test segment presented on the display from the user interface;

determine an awareness level of a test subject based at least in part on the user inputs associated with the cognitive test segment;

determining that the awareness level of the test subject is below a threshold; and re-outputting, at the speaker, the audio associated with the hearing test segment;

re-present the cognitive test segment on a display of the computing device;

re-receive user inputs associated with the cognitive test segment presented on the display from the user interface;

re-determine an awareness level of the test subject based at least in part on the user inputs associated with the cognitive test segment;

determine that the awareness level is above a threshold;

mark the hearing test segment as complete; and display results of the hearing test on the display.

14. The device as recited in claim 13, wherein the hearing test segment is selected based at least in part on at least one of receive an initialization input from the input interface, the initialization input to initiate the hearing test.

15. The device as recited in claim 13, wherein the cognitive test segment is selected based at least in part on at least one of:
 demographic information related to the test subject;
 a time of day; or
 one or more environmental variables.

16. The device as recited in claim 13, wherein outputting audio associated with the hearing test segment includes causing the speaker to output at least one of:
 a test tone;
 a part of speech;
 a phrase; or
 environmental noises.

17. The device as recited in claim 13, wherein the cognitive test segment includes visual information presented on the display.

18. The device as recited in claim 13, further comprising determining each of the plurality of hearing test segments have been marked as completed before outputting the results of the hearing test.

19. The device as recited in claim 13, wherein the non-transitory computer-readable storage media stores additional computer-executable instructions, which when executed by the one or more processors cause the one or more processors to:

receive image data associated with an ear of the test subject after sound damping foam has been placed in an ear canal of the ear; and present on the display, image data associated with an ear of the test subject after sound damping foam has been placed in an ear canal of the ear and at least one image illustrating a correct placement of the sound damping foam within an ear canal.

20. The device as recited in claim 13, further comprising an image device to capture the image data.

* * * * *